US005703033A

United States Patent [19]
Sherry et al.

[11] Patent Number: 5,703,033
[45] Date of Patent: Dec. 30, 1997

[54] LOW SUDSING, LOW STREAKING AND FILMING HARD SURFACE CLEANERS

[75] Inventors: Alan Edward Sherry; Daniel Stedman Connor, both of Cincinnati, Ohio; Robert Emerson Stidham, Lawrenceburg, Ind.; Phillip Kyle Vinson, Fairfield, Ohio

[73] Assignee: The Procter & Gamble Company, Cincinnati, Ohio

[21] Appl. No.: 596,023

[22] Filed: Feb. 6, 1996

[51] Int. Cl.$^6$ ................... C11D 1/28; C11D 1/04
[52] U.S. Cl. ............... 510/237; 510/422; 510/490; 510/501; 510/506; 562/105
[58] Field of Search ................... 510/237, 242, 510/244, 420, 422, 480, 490, 501, 506; 562/105

[56] References Cited

U.S. PATENT DOCUMENTS

| | | | |
|---|---|---|---|
| 2,252,401 | 8/1941 | Jaeger | 260/326 |
| 2,844,608 | 7/1958 | Hagge et al. | 260/401 |
| 3,047,353 | 7/1962 | Klein | 8/86 |
| 3,047,354 | 7/1962 | Owren | 8/86 |
| 3,206,408 | 9/1965 | Vitalis | 252/161 |
| 4,252,657 | 2/1981 | Barriol et al. | 252/8.55 |
| 4,790,856 | 12/1988 | Wixon | 8/137 |
| 5,290,475 | 3/1994 | Wixon | 252/174.23 |
| 5,411,674 | 5/1995 | Tagata et al. | 252/117 |
| 5,480,586 | 1/1996 | Jakubicki et al. | 252/545 |
| 5,591,708 | 1/1997 | Richter | 510/463 |

FOREIGN PATENT DOCUMENTS

| | | |
|---|---|---|
| 509608 | 10/1992 | European Pat. Off. |
| 850878 | 10/1960 | United Kingdom . |
| 1578319 | 11/1980 | United Kingdom . |

*Primary Examiner*—Paul Lieberman
*Assistant Examiner*—John R. Hardee
*Attorney, Agent, or Firm*—Richard S. Echler, Sr.; Kim William Zerby; Brian M. Bolam

[57] ABSTRACT

The present invention relates to low sudsing hard surface cleaning compositions comprising a dianionic sulfosuccinamate and a polyethoxylated alcohol nonionic surfactant which provides non-streaking and non-filming benefits. The compositions of the present invention are effective on clear and colorless, shiny, or "semi-gloss" surfaces.

21 Claims, No Drawings

LOW SUDSING, LOW STREAKING AND FILMING HARD SURFACE CLEANERS

FIELD OF THE INVENTION

The present invention relates to Hard Surface Cleaning compositions comprising a novel sulfosuccinamate in combination with certain nonionic surfactants which together provide low sudsing, non-streaking and non-filming benefits.

BACKGROUND OF THE INVENTION

The main task of hard surface cleaners is to thoroughly and efficiently wash a surface which is in need of cleaning. However, when a film, a residue or streaking is left behind, the success of the cleaning process becomes dubious. Therefore not only must a hard surface cleaner wash the surface in question but it must also leave the surface with the appearance of being cleaned. Although streaks, films and residues are visible to some degree on all smooth or semi-smooth surfaces, they are even more visible on highly reflective or "shiny" surfaces (i.e., glass, ceramic).

It has always been well understood by those skilled in the art of hard surface cleaners that regardless to what degree a surface has been rendered "cleaned" the mere appearance of residues due to the cleaning system will bring into question the efficiency of the cleaning product. Consumers use hard surface cleaners full strength (neat) or in diluted form. When hard surface cleaners are used directly, they can be sprayed right onto the surface, poured onto a sponge or cloth or applied via an attached applicator. When used in diluted form, the cleaner may be poured into a bucket or other container containing water, however both of these cleaning processes can result in the formation of films, streaks, smears or residues.

Surprisingly, it has been found that certain sulfosuccinamate surfactants having a N-2-propylheptyl alkyl moiety when used in combination with selected nonionic surfactants afford hard surface cleaning compositions having greatly improved anti-streaking, anti-filming and anti-residue benefits. The sulfosuccinamates also provide improved neat cleaning performance. In addition, the compounds of the present invention cause soap suds to collapse faster and therefore provide lower sudsing hard surface cleaners. The anti-streaking, anti-filming, and anti-residue benefits of the compositions of the present invention are realized whether the surface to be cleaned is clear and colorless (glass), shiny (ceramic tile, porcelain), or a "semi-gloss" surface (linoleum, polyurethane, Formica,) all of which are typical of materials that comprise flooring, bathroom surfaces, counter tops, etc.

BACKGROUND ART

Various patents and publications refer to sulfosuccinamates, among others; U.S. Pat. No. 2,252,401, Jaeger, issued Aug. 12, 1941; U.S. Pat. No. 2,844,608, Hagge et al., issued Jul. 22, 1958; U.S. Pat. No. 3,047,353, Klein, issued Jul. 31, 1962; U.S. Pat. No. 3,047,354, Owren, issued Jul. 31, 1962; U.S. Pat. No. 4,252,657, Bariol et al., issued Feb. 24, 1981; U.S. Pat. No. 4,790,856, Wixon, issued Dec. 13, 1988; U.S. Pat. No. 5,411,674, Tagata et al., issued May 2, 1995; U.S. Pat. No. 5,480,586, Jakubicki et al., issued Jan. 2, 1996; U.K. Application 850,878, published Oct. 12, 1960; U.K. Application 1,578,319, published Nov. 5, 1980; and EP Application 509,608, published Oct. 21, 1992.

SUMMARY OF THE INVENTION

The present invention relates to hard surface cleaning compositions that provide improved shine and reduced surface streaking and spotting, comprising:

a) at least about 0.1% by weight, of a sulfosuccinamate having the formula

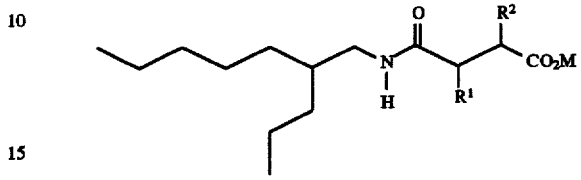

wherein $R^1$ and $R^2$ are hydrogen or $-SO_3M^2$ provided $R^1$ does not equal $R^2$; M and $M^2$ are independently hydrogen or a salt forming cation;

b) at least about 0.1% by weight, of a nonionic surfactant having the formula

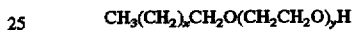

wherein x is from about 6 to about 12, y is from about 3.5 to about 10; and c) the balance carriers and adjunct ingredients.

It is an object of the present invention to provide hard surface cleaning compositions that provide improved shine and anti-streaking benefits.

It is also an object of the present invention to provide hard surface cleaning compositions that provide good filming/streaking properties over a wide range of relative humidity conditions and hard surface compositions.

It is a further object of the present invention to provide hard surface cleaning compositions having improved neat cleaning properties.

It is yet a further object of the invention to provide hard surface cleaning compositions that do not leave the appearance of a film or residue.

It is also an object of the present invention to provide a novel dianionic surfactant, namely N-2-propylheptyl sulfosuccinamate.

All percentages, ratios and proportions herein are by weight, unless otherwise specified. All temperatures are in degrees Celsius (°C.). All documents cited are, in relevant part, incorporated herein by reference.

DETAILED DESCRIPTION OF THE INVENTION

The hard surface cleaning compositions of the present invention provide a surprising benefit of anti-streaking and anti-filming resulting in improved shine and lack of visible residue. In order to achieve this improvement the hard surface cleaning composition must comprise the two following ingredients.

Sulfosuccinamate

The hard surface cleaning compositions of the present invention must comprise the dianionic surfactant N-2-propylheptyl sulfosuccinamate having the formula

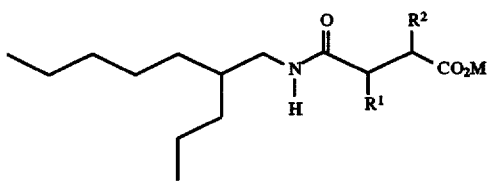

wherein $R^1$ and $R^2$ are selected from hydrogen or the moiety —$SO_3M^2$, provided however that $R^1$ and $R^2$ are not the same, that is when $R^1$ is hydrogen, $R^2$ must be —$SO_3M^2$ and vice versa. M and $M^2$ are independently selected from hydrogen or a salt forming cation. Three carbon atoms in the above molecule are chiral centers, that is they individually have the capacity to form optical isomers or enantiomers. In addition, when two or more of these chiral carbons are taken together they may form diasteriomeric pairs or combinations. For the purposes of the present invention the N-2-propylheptyl sulfosuccinamate is drawn such that each chiral center is shown in its racemic form. For the purposes of the present invention all isomeric forms of N-2-propylheptyl sulfosuccinamate are suitable for use in the compositions of the present invention.

M and $M^2$ may be hydrogen or a salt forming cation depending upon the method of synthesis chosen and the pH of the final hard surface cleaner. Examples of salt forming cations are lithium, sodium, potassium, calcium, magnesium, quaternary alkyl amines having the formula

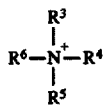

wherein $R^3$, $R^4$, $R^5$ and $R^6$ are independently hydrogen, $C_1$–$C_{22}$ alkyl, $C_4$–$C_{22}$ branched alkyl, C1–$C_6$ alkanol, $C_1$–$C_{22}$ alkenyl, $C_4$–$C_{22}$ branched alkenyl, and mixtures thereof. A different salt forming cation may be chosen for the carboxylate moiety (—$CO_2^-$) than is chosen for the sulfonate moiety (—$SO_3^-$). Preferred cations are ammonium ($R^3$, $R^4$, $R^5$ and $R^6$ equal hydrogen), sodium, potassium, mono-, di-, and trialkanol ammonium, and mixtures thereof. The monoalkanol ammonium compounds of the present invention have $R^3$ equal to $C_1$–$C_6$ alkanol, $R^4$, $R^5$ and $R^6$ equal to hydrogen; dialkanol ammonium compounds of the present invention have $R^3$ and $R^4$ equal to $C_1$–$C_6$ alkanol, $R^5$ and $R^6$ equal to hydrogen; trialkanol ammonium compounds of the present invention have $R^3$, $R^4$ and $R^5$ equal to $C_1$–$C_6$ alkanol, $R^6$ equal to hydrogen. Preferred alkanol ammonium salts of the present invention are the mono-, di- and tri-quaternary ammonium compounds having the formulas:

Preferred M and $M^2$ are hydrogen, sodium, potassium and the $C_2$ alkanol ammonium salts listed above; most preferred are hydrogen and sodium.

Nonionic Surfactant

The hard surface cleaning compositions of the present invention must further comprise a nonionic surfactant having the formula

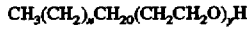

wherein x is from about 6 to about 12, preferably from about 8 to about 10; y is from about 3.5 to about 10, preferably from about 4 to about 7. For the purposes of the present invention the index y refers to the average degree of ethoxylation obtained when contacting a suitable alcohol with a source of ethyleneoxy moieties, and therefore represents all fractional parts within the range 3.5 to 10.

Adjunct Materials

In addition to the above-mentioned required materials, other adjunct ingredients and carriers may be present in the composition. Examples of adjunct ingredients are buffers, builders, chelants, filler salts, dispersants, enzymes, enzyme boosters, perfumes, thickeners, clays, solvents, detersive surfactants, and mixtures thereof. This list is not meant to be totally inclusive or exclusive of materials that are compatible for use in the present invention.

Typically the hard surface cleaning compositions of the present invention will comprise from at least 0.1%, preferably at least 0.5% by weight, of 2-N-propylheptyl sulfosuccinamate and from at least 0.1%, preferably at least 0.5% by weight, a nonionic surfactant having an 8 to 14 carbon alcohol portion and from 3.5 to 10 average units of ethoxylation.

Water is typically used as a filler solvent for "spray on" or "light duty" compositions or to make up the balance of concentrates, however, those skilled in the art can use other compatible solvents such as methanol, isopropanol and the like as solvents, for example when quick drying or low temperature cleaning embodiments are desired. The compositions of the present invention, other than concentrates wherein the consumer adds the carrier prior to use, comprise at least 40%, preferably, at least 45%, more preferably at least 50% by weight, of water as carrier. Concentrates prepared according to the present invention are diluted prior to use to the afore-mentioned concentrations.

The present invention also provides a method for cleaning hard surfaces in need of cleaning wherein the hard surface once cleaned has a decreased amount of visible streaking, spots and residues. The present method comprises the step of contacting the surface in need of cleaning with a hard surface cleaning composition described herein. The method may comprise using the cleaning composition directly (neat) or first diluting the composition in a sufficient amount of water or other carrier.

Further Description of Adjunct Ingredients

As described herein above the compositions of the present invention can optionally include one or more other hard surface cleaning adjunct materials, carriers, solvents or other materials for assisting or enhancing cleaning performance, treatment of the substrate to be cleaned, or to modify the aesthetics of the detergent composition (e.g., perfumes, colorants, dyes, etc.). Common adjunct materials are buffers, builders, chelants, filler salts, dispersants, enzymes, enzyme boosters, perfumes, thickeners, clays, solvents, detersive surfactants, and mixtures thereof, however this list is illustrative and not meant to be limiting or exclusive. The following are illustrative examples of such adjunct materials.

Builders—Builders can optionally be included in the compositions herein to assist in controlling mineral hardness. Preferable are builders that have reduced filming/streaking characteristics at the critical levels of the compositions of the present invention. Addition of specific surfactant builders at critical levels further improves cleaning without the problem of filming/streaking that usually occurs when surfactant builders are added to hard surface cleaners. In light of the improvement displayed by the compositions of the present invention, however, the need for builders to prevent filming and streaking is reduced. Inorganic as well as organic builders can be used.

The level of builder can vary widely depending upon the end use of the composition and its desired physical form.

When present, the compositions will typically comprise at least about 0.1% builder. Liquid formulations typically comprise from about 0.1% to about 5%, more typically about 0.2% to about 2%, by weight, of surfactant builder. Lower or higher levels of builder, however, are not meant to be excluded.

Builders suitable for use in the compositions of the present invention include polycarboxylates and phosphates as well as others cited hereinafter. Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830. issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance due to their availability from renewable resources and their biodegradability. Oxydisuccinates are also especially useful in the compositions and combinations of the present invention.

A preferred polycarboxylate builder is iminodisuccinate. Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Suitable additional optional detergent builders include salts of ethylenediaminetetraacetic acid (hereinafter EDTA), citric acid, nitroacetic acid, (hereinafter NTA), sodium carboxymethylsuccinic acid, sodium N-(2-hydroxypropyl)-iminodiacetic acid, and N-diethyleneglycol-N,N-diacetic acid (hereinafter DIDA). The salts are preferably compatible and include ammonium, sodium, potassium and/or alkanolammonium salts. The alkanolammonium salt is preferred as described hereinafter. A preferred detergent builder are the mixtures citric acid/acetate and bicarbonate/carbonate, more preferred bicarbonate/carbonate.

The additional optional surfactant builders, when present, are typically at levels of from about 0.01% to about 0.5%, more preferably from about 0.02% to about 0.3%, most preferably form about 0.02% to about 0.15%. The levels of these additional builders, present in the wash solution of hard surfaces that comprise glass should be less than about 0.2%.

Chelating Agents—The hard surface cleaning compositions herein may also optionally contain one or more transition metal chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Optional Solvents—Optionally, the compositions of the present invention further comprise one or more solvents. Solvents are broadly defined as compounds that are liquid at temperatures of 20° C.–25° C. and which are not considered to be surfactants. One of the distinguishing features is that solvents tend to exist as discrete entities rather than as broad mixtures of compounds. Solvents of this invention contain from about 1 carbon atom to about 35 carbon atoms, and contain contiguous linear, branched or cyclic hydrocarbon moieties of no more than about 8 carbon atoms. Examples of suitable solvents for the present invention include, methanol, ethanol, propanol, isopropanol, 2-methyl pyrrolidinone, benzyl alcohol and morpholine n-oxide. Preferred among these solvents are methanol and isopropanol.

In a preferred embodiment of the invention, the solvents are selected from the group of compounds comprising ether derivatives of mono-, di- and tri-ethylene glycol, propylene glycol, butylene glycol ethers, and mixtures thereof. The molecular weights of the preferred solvents are less than about 350, more preferably between about 100 and about 300, even more preferably between about 115 and about 250. Examples of preferred solvents include, for example, mono-ethylene glycol n-hexyl ether, mono-propylene glycol n-butyl ether, and tri-propylene glycol methyl ether. Ethylene glycol and propylene glycol ethers are commercially available from the Dow Chemical Company under the tradename "Dowanol" and from the Arco Chemical Company under the tradename "Arcosolv". Other preferred solvents including mono- and di-ethylene glycol n-hexyl ether are available from the Union Carbide company. Preferred solvents according to this invention are present in from about 1% to about 10%, more preferably from about 2% to about 8%, most preferably from about 3% to about 7%, by weight of the hard surface cleaner composition.

Perfumes. Perfumes are an important ingredient for hard surface cleaners, especially those that are used to "refresh" as they clean. Perfume is usually used at levels of from 0% to 2%.

Dyes. Optionally, dyes may be included at levels of from about 0.001% to 0.5%. Examples of suitable dyes are Alizarine Light Blue B (C.I. 63010), Carla Blue VP (C.I. 24401), Acid Green 2G (C.I. 42085), Astrogen Green D (C.I. 42040), Supranol Cyanine 7B (C.I. 42675, Maxilon Blue 3RL (C.I. Basic Blue 80), Drimarine Blue Z-RL (C.I. Reactive Blue 18), Alizarine Light Blue H-RL (C.I. Acid Blue 182), FD&C Blue No. 1 and FD&C Green No. 3. (See the patents of Kitko, U.S. Pat. No. 4,248,827 issued Feb. 3, 1981 and U.S. Pat. No. 4,200,606, issued Apr. 29, 1980, both incorporated herein by reference.) C.I. refers to Color Index.

Polymeric Dispersing Agents—Polymeric dispersing agents can advantageously be utilized at levels from about 0.1% to about 7%, by weight, in the compositions herein. Suitable polymeric dispersing agents include polymeric polycarboxylates, polystyrene sulfonates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued March 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used. Dispersing agents such as polyaspartate preferably have a molecular weight (avg.) of about 10,000.

Detersive Surfactants—The formulator may add other detersive surfactants to the hard surface cleaning compositions of the present invention. Nonlimiting examples of surfactants useful herein typically at levels from about 0.1% to about 20%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("AE$_x$S"; especially EO 1–7 ethoxy sulfates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are listed in standard texts.

The performance of the compositions of this invention are evaluated by means of dilute cleaning, full strength cleaning and dilute shine end result. Outlined below are detailed step by step instructions that explains how each test is conducted. Note that the diluted cleaning test requires two days, as test execution should be conducted after the tiles are allowed to age for about 15 to about 18 hours, For purposes of illustration, dilute cleaning and neat cleaning tests are demonstrated on poly-urethane surfaces, while full strength cleaning is demonstrated on enamel. The test methods are applicable to other surfaces such as ceramic, polyvinylchloride, Formica, parquet, and the like. For shine end result tests, the surfaces are chosen so as to best highlight filming and streaking differences among formulations, i.e., the tests are intentionally performed on shiny black surfaces.

Dilute Cleaning: Method: Sample Preparation on Day 1—Clean four polyurethane coated PVC floor tile panels (Color Tile Nafco ZL-810 No-Wax floor tile cut into 3×12 inch panels) with isopropyl alcohol using delicate task wipers and allow them to dry. If ceramic, poly-vinyl chloride or Formica tiles are used, the same procedures apply.

Prepare greasy particulate soil in sprayer jar consisting of polymerized and un-polymerized oils and particulate matter in a weight ratio of 40:60 Create a dispersion of the model soil in a low boiling inert solvent used to deliver the soil to the tile panels of interest. Stir the dispersion for approximately 30 minutes on a stir plate, occasionally shaking manually. Weigh cleaned floor tile panels; record weight.

Place one tile panel in the back of a fume hood with one of the long edges standing on an easel (long edge parallel to the floor) such that the side to be soiled faces the experimenter. Spray the soil evenly onto the panel (approximately 10–12 strokes) holding the sprayer 12 to 18 inches from the panel. Allow the solvent to evaporate (approximately 30 seconds) and turn the panel 180°. Place the soiled floor tile panels in a fume hood and let dry overnight.

Dilute Cleaning Test: Day 2—Weigh the soiled floor tile panels; record weight. Test water hardness and record.

Dilute Cleaning Test: Execution—Make up test solution: 1X product→7.2 g product/600 g total with water to give a 1.2% product concentration, which corresponds to a 1/64 product dilution; 2X product→3.6 g product/600 g total with water to give a 0.6% product concentration, which corresponds to a 1/128 product dilution.

Place soiled floor tile panel in Gardner Washability machine. Saturate a damp sponge, at 120° F., with 10 ml of the test solution and squeeze out as much test solution as possible with hands. Invert the sponge carrier with sponge and place in the sponge carrier holder so that the saturated side of the sponge will make contact with the soiled floor tile panel to be cleaned. Clean soiled floor tile panel to 100% clean in the Gardner Washability machine. Remove panel; record the number of strokes. Report the amount of soil on each floor tile panel, the average number of strokes to clean and index versus the control(s).

Full Strength (i.e., Neat) Cleaning Test—Clean enamel, ceramic or poly-urethane panels (3×12 inch) are cleaned with isopropyl alcohol and coat with a 2.5 grams kitchen dirt soil, a blend of greasy oil and particulate matter. The panels are baked at 150° C. for about 50 minutes and cooled for at least 1 hour.

Place the soiled enamel panel in an abrasion machine. Place a sponge at 120° F., saturated with water, in a sponge carrier and soak five ml of cleaning formula into the sponge. Place the sponge carrier holder so that the saturated side of the sponge makes contact with the soiled enamel panel to be cleaned. Clean the soiled enamel panel to 100% clean recording the number of strokes necessary to clean the panel. The average number of strokes to clean each panel relates to the efficacy of the full strength cleaning composition.

Shine End Result Test—Clean tiles, rinse with distilled water, and dry with delicate task wipers. Buff tiles using isopropyl alcohol and delicate task wipers so they are free of any marks or streaks. Set test water to 120° F. and desired hardness, record hardness. Rinse filming/streaking sponge with desired test water making sure it is free from any residual test solutions.

Make Up Test Solution 1X product→7.2 g product/600 g total with water of desired hardness to give a 1.2% product concentration, which corresponds to a 1/64 product dilution; 2X product→3.6 g product/600 g total with water of desired hardness water to give a 0.6% product concentration, which corresponds to a 1/128 product dilution.

Saturate a damp filming/streaking sponge with approximately 15 ml of the test solution and tare on a balance. Place the sponge in a sponge carrier. Using the saturated side of the sponge, apply the test solution such that the tile is covered evenly with product using about one gram of the test solution per square foot of surface. Weigh sponge and record weight and relative humidity. Let tiles dry for two to three hours. Grade tiles and index versus the control.

When tested according to the above-described procedures, compositions according to the present invention display increased shine and streaking benefits versus standard hard surface cleaning compositions.

The following non-limiting examples illustrate the invention.

EXAMPLES 1–4

|  | 1 | 2 | 3 | 4 |
|---|---|---|---|---|
| N-2-propylheptyl sulfosuccinamate | 3.0 | 3.0 | 3.0 | 3.0 |
| $C_{11}EO_5$ | 7.0 | 14.0 | 14.0 | — |
| $C_{11}EO_7$ | — | — | — | 7.0 |
| $C_{10}EO_7$ | 7.0 | — | — | 7.0 |
| Trisodium citrate | 1.0 | 1.0 | — | 1.0 |
| Potassium carbonate | 0.2 | 0.2 | 0.2 | 0.2 |
| Triethanol amine | — | — | 1.0 | — |
| Polycarboxylate co-polymer* | — | — | 0.25 | — |
| Perfume | 1.0 | 1.0 | 1.0 | 1.0 |
| Alkalinity adjusted to pH | 10.5 | 10.5 | 7.4 | 10.5 |
| Water, salts, fillers | balance | balance | balance | balance |

*SOKALAN CP-9.

EXAMPLE 5

Preparation of N-2-propylheptyl sulfosuccinamate

To a 10 liter stainless steel reaction vessel equipped with a mechanical overhead stirrer is charged 2-propylheptylamine (235.5 gm, 1.5 mole), acetone (4.0 liter), and water (2 liter). Maleic anhydride (147.0 gm, 1.5 mole) is added slowly with stirring while sufficient 1N NaOH is added to maintain the reaction pH in the range of 7–9. The amount of NaOH necessary is typically 1.5 mole. Continue to stir 10–15 minutes. Sodium bisulfite (171.6 gm, 1.65 mole) is added and the reaction is stirred an additional 10–15 minutes. Typically the solution pH is 8.05. The solution is allowed to stir and additional 2 hours then the contents of the vessel is poured into a convenient container and allowed to solidify as the solvent evaporates to afford 389 gm of a white solid (~68%).

What is claimed is:

1. A hard surface cleaning composition having improved shine and anti-streaking benefits comprising:

a) at least about 0.1% by weight, of a sulfosuccinamate having the formula

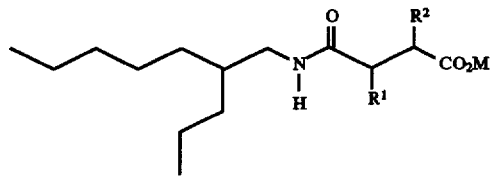

wherein $R^1$ and $R^2$ are hydrogen or $—SO_3M^2$ provided $R^1$ does not equal $R^2$; M and $M^2$ are independently hydrogen or a salt forming cation;

b) at least about 0.1% by weight, of a nonionic surfactant having the formula $CH_3(CH_2)_xCH_2O(CH_2CH_2O)_yH$ wherein x is from about 6 to about 12, y is from about 3.5 to about 10; and c) the balance carriers and adjunct ingredients.

2. A composition according to claim 1 wherein the adjunct ingredients are selected from the group consisting of buffers, builders, chelants, filler salts, dispersants, enzymes, enzyme boosters, perfumes, thickeners, clays, solvents, detersive surfactants, and mixtures thereof.

3. A composition according to claim 1 wherein M and $M^2$ are each independently hydrogen or a water soluble cation selected from the group consisting of sodium, potassium, calcium, magnesium, quaternary alkyl amines having the formula $$R^6-\overset{\overset{\displaystyle R^3}{|}}{\underset{\underset{\displaystyle R^5}{|}}{N^+}}-R^4$$

wherein $R^3$, $R^4$, $R^5$ and $R^6$ are independently hydrogen, C1-C22 alkyl, $C_4$–$C_{22}$ branched alkyl, $C_1$–$C_6$ alkanol, $C_1$–$C_{22}$ alkenyl, $C_4$–$C_{22}$ branched alkenyl, and mixtures thereof.

4. A composition according to claim 3 wherein M and $M^2$ are each independently hydrogen, sodium, potassium, quaternary alkyl amines having the formula $$R^6-\overset{\overset{\displaystyle R^3}{|}}{\underset{\underset{\displaystyle R^5}{|}}{N^+}}-R^4$$

wherein $R^3$ is hydrogen, $R^4$, $R^5$ and $R^6$ are independently hydrogen, $C_1$–$C_6$ alkanol, and mixtures thereof.

5. A composition according to claim 4 wherein M and $M^2$ are each independently hydrogen, sodium, potassium, quaternary alkyl amines having the formula $$R^6-\overset{\overset{\displaystyle R^3}{|}}{\underset{\underset{\displaystyle R^5}{|}}{N^+}}-R^4$$

wherein $R^3$ is hydrogen, $R^4$, $R^5$ and $R^6$ are independently hydrogen, $C_2$ alkanol, and mixtures thereof.

6. A compostion according to claim 5 wherein M and $M^2$ are each independently hydrogen, sodium, and mixtures thereof.

7. A composition according to claim 1 wherein $R^1$ is hydrogen and $R^2$ is —$SO_3M^2$.

8. A composition according to claim 1 wherein $R^1$ is —$SO3M^2$ and $R^2$ is hydrogen.

9. A composition according to claim 1 wherein x is from 8 to 10.

10. A composition according to claim 1 wherein y is from 4 to 7.

11. A composition according to claim 1 comprising at least about 0.5% by weight, of N-2-propylheptyl sulfosuccinamate.

12. A composition according to claim 1 comprising at least about 0.5% by weight, of nonionic surfactant.

13. A sulfosuccinamate compound having the formula wherein $R^1$ and $R^2$ are hydrogen or —$SO_3M^2$ provided $R^1$ does not equal $R^2$; M and $M^2$ are independently hydrogen, a salt forming cation, and mixtures thereof.

14. A compound according to claim 13 wherein $R^1$ is hydrogen and $R^2$ is —$SO_3M^2$; M and $M^2$ are independently hydrogen, salt forming cation, and mixtures thereof.

15. A compound according to claim 1 wherein M and $M^2$ are each independently hydrogen or a water soluble cation selected from the group consisting of sodium, potassium, calcium, magnesium, quaternary alkyl amines having the formula $$R^6-\overset{\overset{\displaystyle R^3}{|}}{\underset{\underset{\displaystyle R^5}{|}}{N^+}}-R^4$$

wherein $R^3$, $R^4$, $R^5$ and $R^6$ are independently hydrogen, $C_1$–$C_{22}$ alkyl, $C_4$–$C_{22}$ branched alkyl, $C_1$–$C_6$ alkanol, $C_1$–$C_{22}$ alkenyl, $C_4$–$C_{22}$ branched alkenyl, and mixtures thereof.

16. A composition according to claim 3 wherein M and $M^2$ are each independently sodium, potassium, quaternary alkyl amines having the formula $$R^6-\overset{\overset{\displaystyle R^3}{|}}{\underset{\underset{\displaystyle R^5}{|}}{N^+}}-R^4$$

wherein $R^3$ is hydrogen, $R^4$, $R^5$ and $R^6$ are independently hydrogen, $C_1$–$C_6$ alkanol, and mixtures thereof.

17. A compound according to claim 16 wherein M and $M^2$ are each independently hydrogen, sodium, and mixtures thereof.

18. A compound according to claim 13 wherein $R^1$ is hydrogen and $R^2$ is —$SO_3M^2$.

19. A compound according to claim 1 wherein $R^1$ is —$SO_3M^2$ and $R^2$ is hydrogen.

20. A method for cleaning hard surfaces, said method comprising the step of contacting a hard surface in need of cleaning with the composition according of claim 1.

21. A method for cleaning hard surfaces, said method comprising the step of contacting a hard surface in need of cleaning with the composition according to claim 1.

* * * * *